United States Patent [19]

Fu

[11] 4,323,467
[45] Apr. 6, 1982

[54] CONTACT LENS CLEANING, STORING AND WETTING SOLUTIONS

[75] Inventor: Cherng-Chyi Fu, Sunnyvale, Calif.

[73] Assignee: Syntex (U.S.A.) Inc., Palo Alto, Calif.

[21] Appl. No.: 209,795

[22] Filed: Nov. 24, 1980

[51] Int. Cl.$^3$ .................. C11D 1/44; C11D 1/66; C11D 1/722; C11D 3/48

[52] U.S. Cl. .................. 252/106; 252/173; 252/529; 252/548; 134/42

[58] Field of Search ............... 252/106, 173, 529, 548; 134/42

[56] References Cited

U.S. PATENT DOCUMENTS

| | | | |
|---|---|---|---|
| 2,674,619 | 4/1954 | Lundsted | 252/548 |
| 3,312,627 | 4/1967 | Hooker | 252/548 |
| 3,337,463 | 8/1967 | Schmolka | 252/529 |
| 3,882,036 | 5/1975 | Krezanoski | 252/106 |
| 3,950,277 | 4/1976 | Stewart | 252/548 |
| 3,954,644 | 5/1976 | Krezanoski | 252/106 |
| 4,046,706 | 9/1977 | Krezanoski | 252/106 |
| 4,104,187 | 8/1978 | Sibley | 252/106 |
| 4,127,423 | 11/1978 | Rankin | 252/106 |
| 4,131,651 | 12/1978 | Shah | 424/78 |

*Primary Examiner*—Dennis L. Albrecht
*Attorney, Agent, or Firm*—James M. Kanagy; Tom M. Moran; Alan M. Krubiner

[57] ABSTRACT

A solution for cleaning, storing or wetting contact lenses which comprises a poly(oxyethylene)-poly(oxypropylene) substituted ethylenediamine surfactant having a molecular weight between 1,600 and 27,000; a germicidal agent; a viscosity builder; a tonicity agent; a sequestering agent and water.

9 Claims, No Drawings

CONTACT LENS CLEANING, STORING AND WETTING SOLUTIONS

BACKGROUND

1. Field of the Invention

This invention relates generally to a solution for cleaning, storing or wetting contact lenses. More specifically, it relates to an aqueous solution containing a poly(oxyethylene)-poly(oxypropylene) substituted ethylenediamine surfactant in admixture with one or more germicide, a viscosity builder, a tonicity agent and a sequestering agent.

2. Prior Art

Contact lens technology and contact lens use has been developing and expanding rapidly since the Second World War. While contact lenses were first proposed as far back as Leonardo Da Vinci and glass lenses were in use during the early part of this century, widespread development and use did not come about until the advent of polymer chemistry in the 1930's and 1940's.

It is usual to classify contact lenses as being hard, flexible, or soft hydrogel depending upon the structural characteristics of the material used to make the lens. A second, and more useful, way of classifying contact lenses would be to designate a particular polymer as having either a hydrophilic or hydrophobic surface. Such a classification system has merit because comfortable wear and visual acuity depend in good part upon the ability of the contact lens to be compatible with the tear fluid which normally exists on the eye surface, particularly the cornea of the eye. Under normal physiological conditions, the surface of the cornea is covered by a thin film of tear fluid. This film contains sebaceous material and polysaccharide conjugated albumin and globulin known as mucin. These materials are not distributed homogeneously throughout the tear layer. Rather, the mucin is concentrated next to the surface of the cornea. Over this concentrated mucin layer is an intermediate watery layer containing highly dilute mucin overlaid with a thin layer of sebaceous material. There is an excess of albumin and globulin in the tear fluid relative to the corneal tissue fluid which produces a lowered surface tension allowing the tear film to spread evenly over the epithelial surface.

To be safe and functional it is necessary that any lens placed on the eye is in some matter completely wetted by this tear layer at all times. Uniform and continuous wetting of the lens by the tear fluid is required for comfortable wear, for providing good optical performance and for preventing the accumulation on the lens of proteinaceous and sebaceous materials.

The majority of contact lenses in use today are either the poly(methylmethacrylate) (PMMA) hard lens or the soft hydrogel lenses. Other recently developed polymers useful for contact lenses include, for example, poly(methylmethacrylate)-silicone materials (PMMA-silicone) marketed as the Polycon ® lens, fluoroalkyl-methylmethacrylate polymers, the cellulose acetate butyrate (CAB) family of polymers, silicone rubber polymers and silicone-polycarbonate polymers. All have been investigated as alternatives to PMMA and soft hydrogel polymers. These new polymers are all hydrophobic. The first two new polymers mentioned above are hard lenses, while the CAB material may be hard or flexible, depending upon the acetyl-butyryl ratio, and the latter two are flexible polymers. A review of current contact lens technology can be found in the *Encyclopedia of Chemical Technology*, Kirk-Othmer, Ed. Vol. 6, 3rd ed. (1979) John Wiley & Sons, pp. 720–742.

Attempts are being made to create a hydrophilic surface on the hard and the flexible hydrophobic contact lenses either by coating them with a hydrophilic material during manufacture or chemically altering the surface to produce a hydrophilic surface or changing a copolymer to provide a hydrophilic material such as the hydrogel lens; but no commercially acceptable materials of this type are available to date. Some means of wetting the hydrophobic surfaces of these new lenses and the old PMMA lenses before insertion onto the eye is required for comfortable and extended wear.

There are several formulations currently known and available commercially which can serve the purpose of wetting the contact lens surface before it is inserted on the eye. Generally these solutions contain a wetting agent in combination with a germicide, some viscosity builder, and salts of some type to adjust the tonicity of the solution to make it compatible with the osmoticity of the tear fluid. The best known of these wetting agents is polyvinyl alcohol, the subject of U.S. Pat. Nos. 3,183,152; 3,549,747 and 4,131,651 in which PVA is used as a wetting agent for hard contact lenses and as a component of artificial tears. Alkylated and hydroxyalkylated cellulose polymers such as hydroxy propylmethylcellulose and methylcellulose have been described as having hydrophobic lens wetting properties but these polymers are used now mainly as viscosity builders and demulcents in conjunction with some other wetting agent such as PVA. See *Remington's Pharmaceutical Sciences*, Arthur Osol Ed. 16th ed. MacK Pub. Co., Easton PA, p. 719 (1980). A third material, having the trademark Pluronic, has been disclosed as a wetting agent for contact lenses in U.S. Pat. Nos. 3,882,036 and 3,954,644. This nonionic surfactant is a poly(oxyethylene)-poly(oxypropylene) block polymer in admixture with preservatives, viscosity agents and tonicity agents. This particular polymer is said also to have cleaning properties because of its surfactant activity.

The poly(oxyethylene)-poly(oxypropylene) substituted ethylenediamine surfactants used as wetting agents herein also are surface-active agents and thus may be used for the cleansing of contact lenses. A number of non-ionic detergents which can be employed to clean contact lenses are disclosed in U.S. Pat. Nos. 3,882,036 and 3,954,644.

None of the above listed references disclose the use of poly(oxyethylene)-poly(oxypropylene) substituted ethylenediamine surfactants as wetting agents for contact lenses or as cleaning agents for the same.

SUMMARY OF THE INVENTION

This invention is drawn to an improved composition for cleaning, storing, or wetting contact lenses, wherein the improvement comprises the addition of a poly(oxyethylene)-poly(oxypropylene) substituted ethylenediamine non-ionic surfactant to a solution for cleaning, storing or wetting a contact lens. The compositions contain the non-ionic surfactant which is the wetting or cleaning agent, at least one germicide, a polymeric viscosity builder, a tonicity agent, a sequestering agent and water. These solutions may be used to clean, store or wet any type of contact lens. More specifically, the solution is composed of a poly(oxyethylene)-poly(oxypropylene) substituted ethylenediamine surfactant of the general formula:

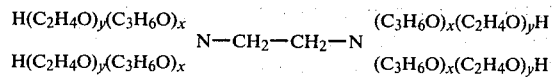

in combination with a germicide such as an organic mercurial compound, or a quaternary amine compound; a water soluble cellulose derived viscosity builder, for example, an hydroxy alkylated cellulose; a tonicity agent, such as a monovalent alkali metal halide salt; a sequestering agent; and the remainder water.

This invention also includes a method for cleaning, storing and wetting a contact lens by treating a lens with a solution disclosed herein. A process for preparing these solution is also disclosed.

DETAILED DESCRIPTION OF THE INVENTION

The wetting and cleaning properties of the solutions of this invention are achieved by the use of polymeric, non-ionic surfactants. These surfactants are physiologically acceptable and chemically compatible polyalkylene substituted ethylenediamine polymers. These surfactants, sold under the trademark Tetronic ®, are a series of closely related polymers consisting of poly(oxyethylene)-poly(oxypropylene) block polymers substituted on the nitrogens of an ethylenediamine molecule. They may be represented by the general formula:

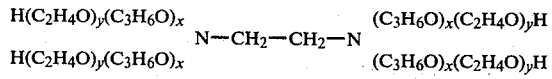

and are the subject of U.S. Pat. No. 2,979,528. Their preparation can be found in that patent which is incorporated herein by reference.

These polymers are surface active agents because of the presence of poly(oxypropylene) groups, which are hydrophobic, in conjunction with hydrophilic poly(oxyethylene) groups. The hydrophobic-hydrophilic properties of a particular polymer are controlled by varying the percentage by weight of the poly(oxyethylene) hydrophilic groups present in a polymer. Poly(oxyethylene) may constitute from 10-80% of the total molecular weight of a particular polymer. In a molecule with only 10% poly(oxyethylene) the hydrophobic poly(oxypropylene) characteristic will dominate, while a polymer with 80% poly(oxyethylene) will show pronounced hydrophilic characteristics.

Tetronic ® polyols are commercially available as a group of twenty-one different polymers which fall into a broad molecular weight range beginning at approximately 1,600 and going up to 27,000. Each polymer's hydrophilic-hydrophobic balance varies by a slight increment from the other, depending on the percentage of poly(oxyethylene) in the polymers. They may be liquids, pastes or flakable solids, depending on their molecular weight and poly(oxyethylene) content. All exhibit good surface tension lowering properties, can act as detergents and have a low order of toxicity and eye irritation.

All the Tetronic ® polyols are useful as cleaning and wetting surfactants in contact lens cleaning and wetting solutions but particular physical and chemical characteristics of certain of these polyols make their use more desirable in this invention. Since all members of the series demonstrate good wetting ability, adequate detergent characteristic, low toxicity and, for the most part, are non-irritants to eye tissue, specific polymers were chosen based on their cloud point. The temperature at which a given concentration of polymer begins to form waxy solids as the solution is cooled is called its cloud point. Since waxy solids in the cleaning and wetting solutions could interfere with their use and function, only those Tetronic ® polyols showing a cloud point in excess of 50° C. for a 10% aqueous solution are preferred in this invention. Table I lists these polymers along with their molecular weight and cloud point according to the code use by BASF Wyandotte and their CTFA designation.

TABLE I

| Tetronic ® | CTFA* Name | Typical Molecular Weight | Cloud Point °C. of 10% solution |
|---|---|---|---|
| 304 | 304 | 1650 | 73 |
| 504 | 504 | 3400 | 70 |
| 704 | 704 | 5500 | 66 |
| 707 | 707 | 12000 | 100 |
| 904 | 904 | 7500 | 66 |
| 908 | 908 | 27000 | 100 |
| 1104 | 1104 | 8300 | 69 |
| 1107 | 1107 | 14500 | 100 |
| 1304 | 1304 | 10500 | 75 (gel) |
| 1307 | 1307 | 18600 | 100 |
| 1504 | 1504 | 12500 | 75 (gel) |
| 1508 | 1508 | 27000 | 100 |

*CTFA Cosmetic Ingredient Dictionary, 2nd ed., Pub. The Cosmetic, Toiletry and Fragrance Association, Washington D.C. (1977).

Out of this group the polymers designated 1104 and 1304 are most preferred. Combinations of these two polymers or of any of the tetronic polymers provide workable solutions but this invention uses only a single polymer per composition.

The cleaning and wetting functions of these solutions can be achieved when the surfactant is present in a non-irritating amount and which is of 0.01% to 40% by weight of the solutions. While this broad range of concentrations will achieve the desired results, solutions containing 0.1% to 15% of the surfactant are particularly effective, but preferably they will be formulated to contain 0.5% to 1.5% by weight of the solution.

To avoid eye infections from contaminated contact lenses it is necessary to include one or more germicidal agents in contact lens cleaning, storage and wetting solutions.

Contact lenses can pick up pathogens from many sources. One possible source of bacteria contamination is the cleaning and wetting solution itself, when stored in multiple use containers. Normally the manufacturing process will provide a sterile cleaning and wetting solution in a container sealed to prevent contamination during storage and transport. Solutions packaged in single use containers present no subsequent sterility problems but by far the majority of contact lens solutions are available in multiple use containers. Once the seal is broken on multiple use containers, bacterial infestation may occur regardless of how careful the user may be. Therefore some means for arresting and controlling bacterial, fungal and viral growth in a multiple use container is required.

A second source of contamination is the environment of the eye. Microbial growth on the eye surface is normally controlled by lysozymes present in the tear fluid. These materials kill microbes by enzymatically degrading their cell wall structures. However a contact lens may be contaminated at the time it is removed from the eye by spores or microbes which had for some reason not been inactivated by the lysozymes. If these spores or microbes are not effectively controlled and eliminated during the cleaning and storage process they could infect the eye when the lens was reinserted at a later time. Lenses may also pick up pathogens from the hands, from the cleaning instruments or, during storage, from the container itself; or by infestation, especially during long-term storage where a volatile germicide is used.

Because hydrophobic lenses absorb very little water (0.1-4%), they are incapable of absorbing most germicidal agents from cleaning and storage solutions; so a wide variety of germicidal agents of known activity may be effectively used in the solutions of this invention. There may be used, for example, such germicidal agents as quaternary amines, organic mercurial compounds, sorbic acid, polymyxin B sulfate, chloralbutanol, parabens and phenols, to name some of the germicides generally used in opthalmic solutions. Herein it is preferred to use an organic mercurial compound alone or in combination with a quaternary amine for maintaining the sterility of bottled solutions as well as for sterilizing lenses during the cleaning and storage process. One preferred formulation would include the organic mercurial compound, thimerosal, chemically known as ethyl(2-mercaptobenzoato-S)mercury sodium salt. An alternative and equally preferred method for controlling microbial growth would be to use the above mentioned thimerosal in conjunction with a quaternary amine germicide, particularly benzalkonium chloride. Benzalkonium chloride is an alkyl substituted dimethylbenzylammonium chloride compound in which the alkyl substituents are a mixture of C8-C18 alkyl radicals.

The solutions disclosed in this invention will contain an amount sufficient to control or arrest the growth of bacteria, fungus, viruses, or other microorganisms in bottled solutions or on stored lenses. Generally this amount is in the range of 0.0005%-0.05%. But it is preferred that the germicide concentration be between 0.001% and 0.02%. Where thimerosal is used alone, it is most preferred that it be present in a concentration of 0.004%. When thimerosal and benzalkonium chloride are used together it is most preferred to have a thimerosal concentration of 0.001% and a benzalkonium chloride concentration of 0.01%.

A sequestering agent is included in these solutions for two reasons. One is to enhance the effectiveness of the germicide benzalkonium chloride. Secondly the sequestering agent can form water soluble complexes with bivalent and trivalent metal ions which otherwise could react with macromolecules such as proteins or long-chain fatty acids to form insoluble precipitates which could collect on the contact lens making subsequent cleaning additionally difficult.

A wide range of organic acids, amines or compounds which include an acid group and an amine function are capable of acting as sequestering compounds. For example, nitrilotriacetic acid, diethylenetriaminepentaacetic acid, hydroxyethylethylenediaminetriacetic acid, 1,2-diaminocyclohexane tetraacetic acid, hydroxyethylaminodiacetic acid, ethylenediaminetetraacetic acid and its salts, polyphosphates, citric acid and its salts, tartaric acid, and the like, are useful sequestering agents. Ethylenediaminetetraacetic acid and its alkali metal salts, are generally preferred for use in ophthalmic solutions. It is most preferred to use the disodium salt of ethylenediamenetetraacetic acid, also known as disodium edetate.

The sequestering agent is present in an amount sufficient to achieve the purposes set forth above which generally will be between 0.01% and 1% by weight of the solution, but preferably it will be present in an amount of between 0.05% and 0.5%. Solutions prepared according to the teachings of this invention will normally include the sequestering agent in an amount of 0.1%.

A water-soluble viscosity builder is included in the disclosed solutions to prolong the wetting activity of the surfactant and to act as a demulcent. By increasing the viscosity of the solution, the film formed on the lens will be less subject to being sluffed off by lens movement over the corneal surface during the blinking motion. Maintaining the surfactant on the lens surface for a longer period of time enhances wearer comfort and increases wearability. A viscosity builder can also act as a demulcent, thereby cushioning the impact of the lens on the eye surface during insertion and serving also to alleviate eye irritation.

Acceptable viscosity builder are water soluble natural gums and cellulose-derived polymers. Natural gums such as guar gum, gum tragacanth, gelatin and water soluble starch derivatives can be used. The water soluble, cellulose derived viscosity builders are cellulose polymers such as hydroxypropyl cellulose, hydroxypropyl methyl cellulose, carboxymethylcellulose, methyl cellulose, hydroxyethyl cellulose and the like. As will serve equally well as a viscosity builder. The desired viscosity properties of these solutions herein can be best obtained using a cellulose polymer, most preferably hydroxyethyl cellulose.

A sufficient amount of the viscosity builder is added to the solution to achieve a viscosity of about 15-750 CPS at 25° C. A viscosity of about 60 CPS at 25° C. is considered optimum. To achieve this range of viscosity readings an amount of viscosity builder of about 0.01%-5%, depending upon the builder chosen, should be used. The use of 0.1%-1% viscosity builder will produce an acceptable viscosity reading, but the optimum viscosity can be achieved using about 0.5% of the preferred hydroxyethyl cellulose.

Various viscosity grades of cellulose polymers are available commercially. However it is most beneficial to use a medium viscosity cellulose builder to achieve the desired viscosity in the solution of this invention. An example of such a viscosity builder is M grade hydroxyethyl cellulose, available from Hercules, Inc., under the trademark Natrosol. This information is set forth as exemplary only and it should be understood that other cellulose polymers and other viscosity grades thereof can be used as viscosity builders in the solutions of this invention. Natrosol polymers of viscosity grades H, G and J from Hercules or Cellosize WP4400 from Union Carbide Corp., and various other commercially available hydroxyethyl cellulose polymers can be used. The preferred grade of hydroxyethyl cellulose used in these solutions is Natrosol 250 M which can be obtained commercially from Hercules.

Ophthalmic solutions are generally formulated to contain neutral solutes in an amount which will give a solution having approximately the same osmotic value as that of normal tear fluid. These solutes are called tonicity agents herein. Tonicity refers to the osmotic pressure of a solution vis-a-vis some physiological fluid, here tear fluid. The osmotic value of tear fluid is equivalent to a sodium chloride concentration of 0.9%, although sodium chloride constitutes only approximately 0.65% of tear fluid. While fluids placed on the eye can deviate substantially in osmotic value from that of tears, it is preferred to provide a wetting and cleaning solution which is isotonic or slightly hypertonic in relation to tear fluid. Although the tonicity of the wetting and cleaning solution can vary between 0.5% and 1.8% without adversely effecting the eye, it is preferred to maintain the tonic value of these solutions somewhere between 0.6% and 1.1% but, most preferably, at 0.9%.

Various solutes can be used to obtain the desired tonic value in ophthalmic solutions. For instance, polyols such as glycerol and low molecular weight polyethylene glycols can be used. Neutral salts such as monovalent alkali metal halide salts may be used. For example, sodium chloride, sodium bromide, potassium fluoride, potassium chloride, or potassium bromide. There may also be used sodium sulphate, potassium sulphate, sodium nitrate, sodium phosphate, potassium nitrate or potassium phosphate. Alkali metal halide salts are preferred, most particularly sodium chloride, potassium chloride or a combination of the two.

The osmotic value of tear fluids is approximated in the solutions herein by adding at least one tonicity agent in an amount ranging from 0.4% and 1.7%, but preferably in the range of 0.6% to 1.1%. Most preferred are those solutions wherein sodium chloride has been added in an amount of 0.8%. This amount of salt, when combined with the amount of sequestering agent set out above, approximates the preferred tonic value noted above.

Water is used to dilute the non-aqueous ingredients to the final concentration desired. The water is preferably purified by some means such as ultra-filtration, deionization, treatment with charcoal or otherwise sterilized or purified before being used as a diluent.

Water is added by weight in a quantity sufficient to bring the value of these solutions to unity, that is to 100%. The exact quantity of water used will vary depending upon the amount of non-aqueous ingredients to be included in a particular formulation. It should be understood that all percentages listed herein are on a weight/weight basis.

Tetronic ® polyols disclosed herein as wetting agents also have utility for removing soilants from contact lenses. All the solutions described above are capable of effectively removing proteins, fats, mucopolysaccharides and other soilants that may accumulate on lenses during normal wear. The disclosed solution also may be used for storing hydrophobic contact lenses, as sufficient germicidal agents are included in these solutions to arrest and prevent bacterial growth on any contact lenses after cleaning and during storage.

A typical cleaning regime would call for cleaning the lenses 2-10 times per week using these solutions. Cleaning the lens would involve placing several drops of the cleaning solution on the lens surface and gently rubbing the lens between the forefinger and thumb or two fingers for upward of twenty rotations and then rinsing the lens with tap water to remove the cleaning solution and suspended soilents. The lens may then be stored in the same cleaning solution for later use.

Solutions of this invention are prepared according to a general procedure wherein the tonicity agent is blended with the viscosity builder which is then stirred into heated water, after which the wetting agent and the remaining ingredients are added to the pot. To properly dissolve the viscosity builder it is necessary to pre-heat the water above 50° C., preferably 80° C., before mixing in the tonicity agent/viscosity builder mix. After mixing, the solution is sterilized and optionally cooled to room temperature and diluted with sterile water to give the desired final concentration. This solution is then packaged without further treatment.

The following examples are set forth to give a bettter and more complete understanding of the invention contained herein.

EXAMPLE I

A cleaning, storing and wetting solution for contact lenses is prepared having the following composition:

| Solution | Percentage |
| --- | --- |
| Tetronic ® 1304 | 1.5% |
| Thimerosal | 0.004% |
| Hydroxyethyl cellulose | 0.5% |
| Sodium chloride | 0.8% |
| Disodium edetate | 0.1% |
| Water QS | 100% |

The solution was prepared by mixing the sodium chloride with the hydroxyethyl cellulose, stirring this mixture into water at about 80° C., and adding the remaining ingredients. The solution was sterilized and after being cooled to room temperature, sufficient sterile water was added to achieve the concentrations stated in Example I.

This solution had a surface contact angle of 50° when applied to a polymethylmethacrylate-silicone lens (Polycon ®) and a surface tension of 38 dynes/cm.

A Polycon ® lens was dipped in this solution, the excess drained away, and the lens inspected for a continuous film. If such a film covered the entire lens, the lens was dipped momentarily in a beaker of water and again inspected for film continuity. This procedure was repeated until the film was no longer continuous. The number of dippings required to induce film break-up was 25, indicating this formulation functions well as a wetting agent.

This solution was tested for cleaning efficiency. Polycon ® lenses were artificially soiled with a mixture of 87% white petrolatum, 4.3% cholesterol and 8.7% soybean lecithin. Several drops of the Example I solution were applied to the lenses, which were then gently rubbed between the fingers for about twenty times and rinsed with tap water. This solution effectively removed the fatty-cholesterol deposits from the lenses.

EXAMPLE II

The following composition is set out as another example of a wetting and cleaning solution based on Tetronic ® polyols. The formulation of the composition is as follows:

| Solution | Percentage |
| --- | --- |
| Tetronic ® 1104 | 0.5% |
| Thimerosal | 0.001% |
| Hydroxyethyl cellulose | 0.5% |
| Sodium chloride | 0.8% |
| Disodium edetate | 0.1% |
| Benzalkonium chloride | 0.01% |

-continued

| Solution | Percentage |
| --- | --- |
| Water QS | 100% |

This solution was prepared in the same manner as the solution of Example I.

This solution showed a contact angle of 54° on Polycon ® lenses and a surface tension of 38 dynes/cm.

In the film-forming property testing procedure described above under Example I, the lens wetted with this solution underwent film break-up after six dips in water demonstrating that this solution will function adequately as a wetting agent.

The cleaning properties of this solution were tested in the same manner as used in Example I. Fatty-cholesterol deposits were effectively and completely removed from the lenses by this solution.

EXAMPLE III

| Solution | Percentage |
| --- | --- |
| Tetronic ® 1304 | 12.0% |
| Thimerosal | 0.004% |
| Hydroxyethyl cellulose | 0.5% |
| Sodium chloride | 0.8% |
| Disodium edetate | 0.1% |
| Water QS | 100% |

EXAMPLE IV

| Solution | Percentage |
| --- | --- |
| Tetronic ® 1304 | 0.01% |
| Thimerosal | 0.004% |
| Hydroxyethyl cellulose | 0.5% |
| Sodium chloride | 0.8% |
| Disodium edetate | 0.1% |
| Water QS | 100% |

Examples III and IV were prepared in the same manner as described under Example I.

The discussion of the various components of these solutions, their action, usage and amounts is intended to be exemplary and explanatory but should not be considered restrictive in any way of the various combinations and usages which can be made of this invention.

What is claimed:

1. A contact lens cleaning, storing or wetting solution which comprises:
   (a) a poly(oxyethylene)-poly(oxypropylene) substituted ethylene diamine nonionic surfactant which is present in an amount of 0.01% to 40% by weight/volume (w/v);
   (b) at least one germicide which is present in an amount of 0.0005% to 0.05% (w/v);
   (c) a water soluble, cellulose-derived viscosity builder which is present in an amount of 0.01% to 5.0% (w/v);
   (d) at least one tonicity agent which is present in an amount of 0.4% to 1.7% (w/v);
   (e) a sequestering agent which is present in an amount of 0.01% to 1.0% (w/v); and
   (f) water.

2. The composition of claim 1 wherein:
   (a) said surfactant has a cloud point in excess of 50° C. for a 10% solution;
   (b) said germicide is an organic mercurial compound or a quaternary amine compound;
   (c) said viscosity builder is hydroxymethylcellulose, hydroxyethyl cellulose, methylcellulose, hydroxypropyl methylcellulose or sodium carboxymethylcellulose;
   (d) said tonicity agent is an alkali metal halide;
   (e) said sequestering agent is ethylenediaminetetraacetic acid or the salts thereof; and
   (f) water.

3. The composition of claim 2, wherein:
   (a) said surfactant is present in an amount of 0.1% to 15%;
   (b) said germicide is present in an amount of 0.001% to 0.02%;
   (c) said viscosity builder is present in an amount of 0.1% to 1.0%;
   (d) said tonicity agent is present in an amount of 0.6% to 1.1%;
   (e) said sequestering agent is present in an amount of 0.05% to 0.5%; and
   (f) water in a quantity sufficient to bring total composition to unity.

4. The composition of claim 3, wherein:
   (a) said surfactant has a CTFA designation of 1304 and a molecular weight of 10500;
   (b) said germicide is thimerosal;
   (c) said viscosity builder is hydroxyethyl cellulose;
   (d) said tonicity agent is sodium chloride;
   (e) said sequestering agent is disodium ethylenediaminetetraacetic acid; and
   (f) deionized, sterilized water.

5. The composition of claim 4, wherein:
   (a) said surfactant is present in the amount of 1.5%;
   (b) said germicide is present in the amount of 0.004%;
   (c) said viscosity builder is present in the amount of 0.5%;
   (d) said tonicity agent is present in the amount of 0.8%;
   (e) said sequestering agent is present in the amount of 0.1%; and
   (f) water in a quantity sufficient to bring the total composition volume to unity.

6. The composition of claim 3, wherein:
   (a) said surfactant has a CTFA designation of 1104 and a molecular weight of 8300;
   (b) said germicide is thimerosal and benzalkonium chloride;
   (c) said viscosity builder is hydroxyethylcellulose;
   (d) said tonicity agent is sodium chloride;
   (e) said sequestering agent is disodium ethylenediaminetetraacetic acid; and
   (f) deionized, sterile water.

7. The composition of claim 6, wherein:
   (a) said surfactant is present in the amount of 0.5%;
   (b) said germicide thimerosal is present in the amount of 0.001% and benzalkonium chloride is present in the amount of 0.01%;
   (c) said viscosity builder is present in the amount of 0.5%;
   (d) said tonicity agent is present in the amount of 0.8%;
   (e) said sequestering agent is present in the amount of 0.1%; and
   (f) water in a quantity sufficient to bring the total composition to unity.

8. A process for cleaning, storing or wetting a contact lens which comprises contacting the surface of a lens with the composition of claim 1.

9. A process for preparing the composition of claim 1 which comprises:
(a) mixing the tonicity agent with said viscosity builder;
(b) stirring this mixture into hot water;
(c) adding the remaining ingredients to this aqueous mixture;
(d) sterilizing the solution; and
(e) diluting to the desired final concentration by the addition of sterile water.

* * * * *